United States Patent [19]
Sanders et al.

[11] Patent Number: 5,481,197
[45] Date of Patent: Jan. 2, 1996

[54] HIGH PRESSURE, LEAK RESISTANT EXPLOSIONPROOF CAPACITANCE PROBE

[75] Inventors: Gary G. Sanders, Rock Falls; Brian C. Gorge, Moline; Burt L. Beach, Prophetstown, all of Ill.

[73] Assignee: Penberthy, Inc., Prophetstown, Ill.

[21] Appl. No.: 122,849

[22] Filed: Sep. 17, 1993

[51] Int. Cl.⁶ .................................................. G01F 23/26
[52] U.S. Cl. .................... 324/690; 73/304 C; 340/620
[58] Field of Search ........................... 73/290 R, 304 C; 324/658, 663, 684, 690; 340/620; 361/284

[56] References Cited

U.S. PATENT DOCUMENTS

| | | |
|---|---|---|
| 3,262,032 | 7/1966 | Levine et al. . |
| 4,252,993 | 2/1981 | Beaman ................. 73/304 C |
| 4,574,328 | 3/1986 | Maier ..................... 361/284 |
| 4,594,892 | 6/1986 | Asmundsson ........... 73/304 C |
| 4,806,847 | 2/1989 | Atherton et al. ........ 324/678 |
| 4,809,129 | 2/1989 | Hansen, III et al. .... 73/304 C |
| 5,187,979 | 2/1993 | Edmark, III ............. 324/690 |

FOREIGN PATENT DOCUMENTS

| | | |
|---|---|---|
| 101580 | 2/1984 | European Pat. Off. . |
| 1648163 | 4/1970 | Germany . |

*Primary Examiner*—Kenneth A. Wieder
*Assistant Examiner*—Christopher M. Tobin
*Attorney, Agent, or Firm*—Jenner & Block

[57] ABSTRACT

A low intrinsic capacitance probe system for measuring capacitance to detect the liquid fill level of a pressure vessel that incorporates a high pressure center rod retention system and an explosionproof flame path seal into its mounting gland. The system reduces or eliminates the cold flow of PTFE within the probe and eliminates the need for periodic retorquing.

19 Claims, 3 Drawing Sheets

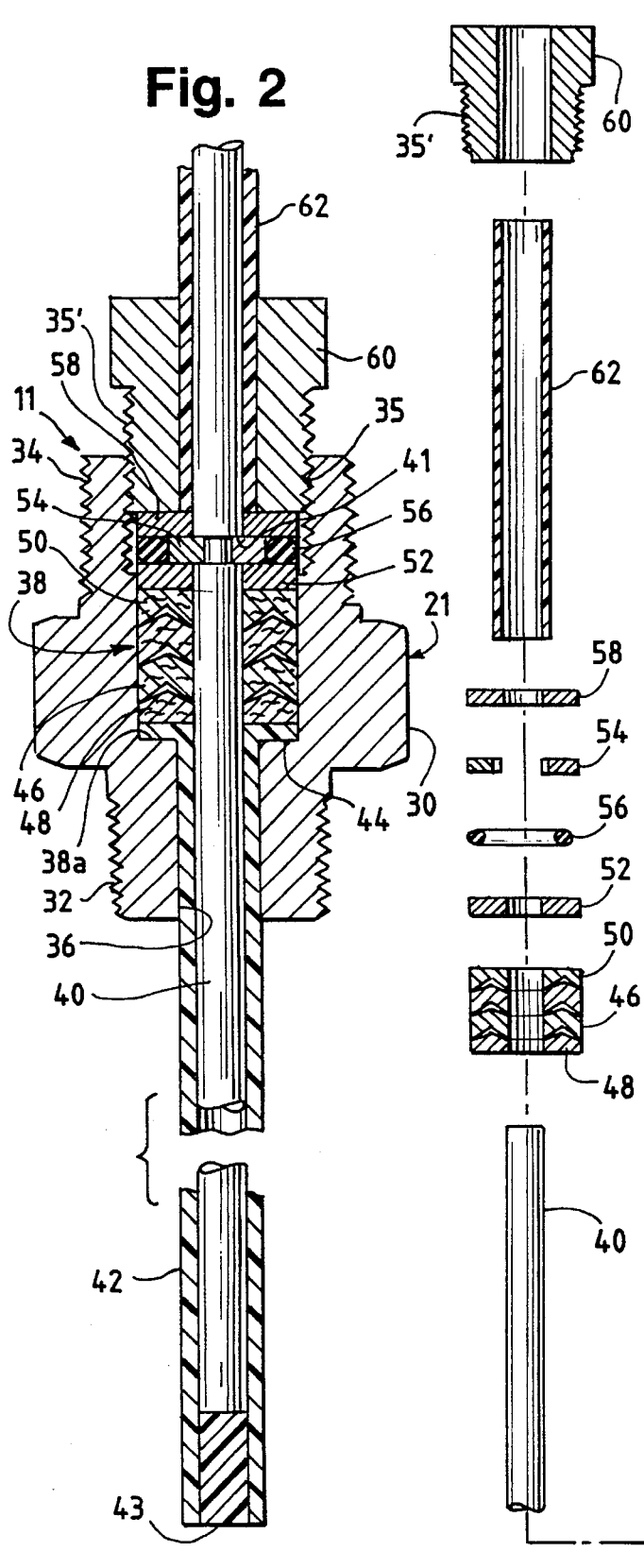
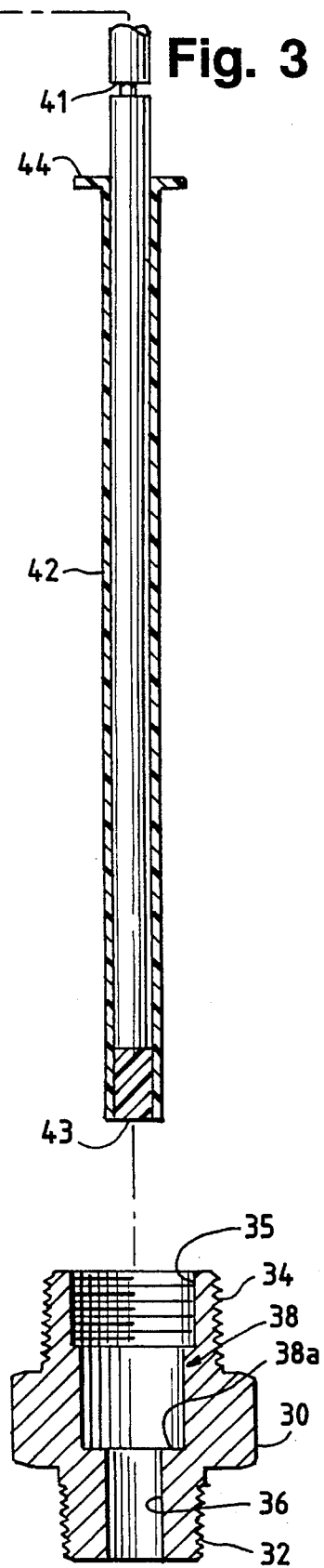

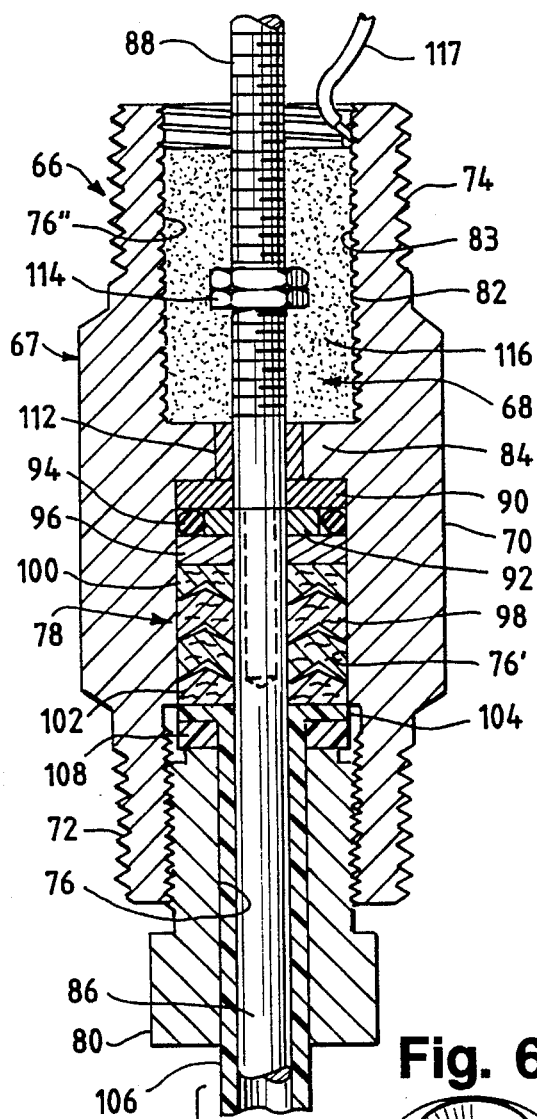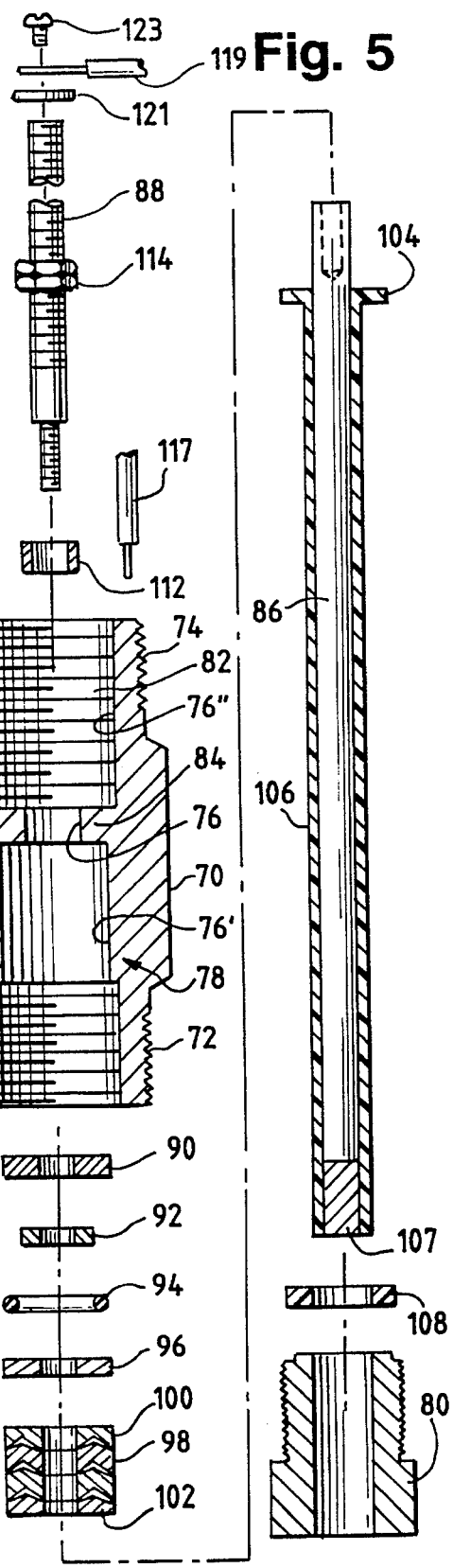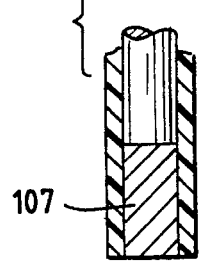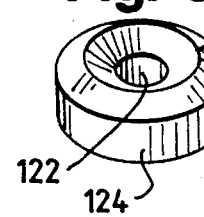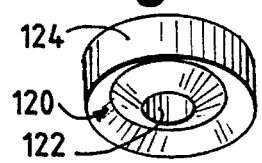

HIGH PRESSURE, LEAK RESISTANT EXPLOSIONPROOF CAPACITANCE PROBE

BACKGROUND OF THE INVENTION

1. Field of the Invention

The invention relates to probes and probe bodies for measuring a desired parameter, such as capacitance. More particularly, the invention relates to a capacitance probe and probe body of the type used for measuring capacitance to detect the level of liquid in a pressure vessel, and still more particularly, to such a probe that resists leakage and, in one embodiment, is explosionproof.

2. Description of the Related Art

In industrial metrology, capacitance commonly is used to determine the level of liquid in vessels, particularly in closed vessels. One method of measuring capacitance is through the use of a concentric-type plate capacitor. A concentric-type plate capacitor utilizes a conductive probe as the center plate of a coaxial capacitor. This conductive probe is usually a cylindrical metal rod (center or probe rod) that is insulated to measure conductive liquid levels. The vessel walls typically form the second plate of the capacitor while the liquid to be measured is the dielectric. The capacitance of a concentric-type plate capacitor is given by the equation:

$$C = \frac{2 \times \pi \times \epsilon \times L}{\ln\left[\frac{r_0}{r_1}\right]}$$

where C=capacitance;

$\epsilon$=dielectric constant (1.000590 for air);

L=length of concentric immersion by the probe rod;

$r_0$=radius of the inside of the outer wall of the vessel; and $r_1$=radius of the metallic probe rod.

The presence of material in the vessel creates a concentric-type plate capacitor with the liquid serving as the dielectric. Therefore, if one knows the dielectric constant of the material in the vessel, by measuring the capacitance, C, it is possible to determine the level of material in the vessel. The probe is connected via suitable electrical connections to capacitance-measuring circuitry. In measuring the capacitance, a lower intrinsic capacitance of the capacitance probe itself is desirable in order to more accurately gauge changes in the overall capacitance that are caused by changes in the liquid level.

Typical capacitance probes use metallic mounting glands to mount the probe rod to the vessel and to the electronics housing. The internal portion of the mounting gland contains: (1) a pressure sealing system; and (2) a probe rod retaining system. The probe rod itself is typically a metallic rod sheathed in polytetrafluoroethylene (PTFE) or other suitable polymer. The probe rod must pass through the metallic mounting gland with no metallic contact.

Referring to FIG. 1, an existing capacitance probe includes a packing gland 10 that is threaded into a mounting gland 12. A center rod or probe rod 14 extends from an electronics housing (not shown) through metal packing gland 10 and mounting gland 12 and into a vessel (not shown). Center rod 14 comprises an upper rod 13 that is threaded into a lower rod 15. Because mounting gland 12 is electrically connected to the vessel walls, center rod 14 must be electrically insulated from mounting gland 12 to achieve an accurate capacitance reading. Therefore, a lower sheath 16 surrounds lower rod 15 and an upper sheath 17 surrounds upper rod 13. Sheaths 16 and 17 are typically composed of PTFE although other polymers may be used. A solid PTFE cap or plug 19 insulates the end of lower rod 15 and is joined to lower sheath 16 thermally.

Housed inside mounting gland 12 is a packing preform 18 that is compressed against lower sheath 16 to form a pressure seal. Packing preform 18 comprises an upper portion 20 and a lower portion 22. Threading on packing gland 10 and mounting gland 12 allows packing gland 10 to be torqued and tightened against packing preform 18 via a PTFE washer 26 and a metallic washer 28. When packing gland 10 is tightened, lower portion 22 of packing preform 18 applies pressure against lower sheath 16 to create a radial pressure seal.

PTFE and other polymers, however, cold flow under pressure. Thus, lower sheath 16 cold flows in the area that is engaged with lower portion 22 of packing preform 18. This cold flow reduces the pressure seal and allows leakage. Deformation also occurs above and below metallic washer 24 in lower sheath 16 and upper sheath 17.

These deformations require periodic retorquing of packing gland 10 to maintain compression. As this retorquing process is repeated, lower sheath 16 flows to the point of separation and the seal fails.

A second difficulty encountered with capacitance probes is the maintenance of center rod 14 against hydrostatic end forces. To solve this problem, existing capacitance probes include one or more metallic washers 24 placed in a groove at a threaded junction point in center rod 14 located within mounting gland 12. Packing preform 18 is made as two separate pieces rather than one in order to facilitate encapsulation of metallic washer 24. Hydrostatic pressure acts against metallic washer 24 in an upward direction forcing it against upper portion 20 of packing preform 18. Although center rod 14 is contained because the outer diameter of metallic washer 24 is greater than the inner diameter of packing gland 10, cold flow of upper portion 20 may occur. Thus, a capacitance probe capable of reducing or eliminating cold flow of the capacitance probe's PTFE is desirable.

In addition, a need exists for a capacitance probe and probe body that is explosionproof under the standards promulgated by the National Fire Protection Association in The National Electrical Code® Handbook (5th ed.).

Finally, a probe and mounting gland apparatus having a lower intrinsic capacitance is desirable because it is difficult to offset large intrinsic capacitances.

SUMMARY OF THE INVENTION

In accordance with the present invention, a capacitance probe and probe body is provided. In accordance with another aspect of the invention, an explosionproof capacitance probe and probe body is provided.

In accordance with one embodiment of the invention, a capacitance probe is provided that includes a mounting gland having a longitudinal bore extending therethrough. The longitudinal bore has a nominal diameter and an enlarged portion, the enlarged portion defining a stuffing box and a stuffing box bottom. A metallic center rod extends through the bore of the mounting gland and an insulating sheath surrounds a lower portion of the center rod and extends into the stuffing box. Structure is provided for sealing the stuffing box between the center rod and the mounting gland and for electrically insulating the center rod from the mounting gland. Structure is also provided for preventing longitudinal movement of the center rod relative to the mounting gland.

The structure for sealing the stuffing box can be composed of a plurality of compression deformable chevron packing rings constructed of a suitable material, such as PTFE, contained in the stuffing box coaxial to the bore and surrounding a longitudinal portion of the rod. Structure is provided for compressing the chevron packing rings against the stuffing box bottom, such as by a packing gland threadably secured to the mounting gland and extending into the stuffing box.

The structure for preventing longitudinal movement can include a circumferential groove in the center rod where the rod is disposed in the stuffing box and a retaining washer disposed in the circumferential groove, with the retaining washer having a larger outer diameter than the nominal diameter of the bore.

In accordance with another embodiment of the invention, an explosionproof capacitance probe is provided. The explosionproof capacitance probe is composed of a mounting gland having a longitudinal bore extending therethrough, the mounting gland having a cavity coaxial to the bore and a stuffing box at the other end of the mounting gland coaxial to the bore and longitudinally spaced from the cavity by a mounting gland center web. Explosionproof sealing structure is provided for sealing the cavity to provide a flame path seal in the cavity. A metallic center rod extends through the bore with an insulating sheath surrounding a lower portion of the center rod. Structure is provided for sealing the stuffing box between the center rod and the mounting gland and for electrically insulating the center rod from the mounting gland. Structure is also provided for preventing longitudinal movement of the center rod relative to the mounting gland.

In one embodiment, the structure for sealing the stuffing box is composed of a plurality of compression deformable chevron packing rings located in the stuffing box and coaxial to the bore and surrounding a longitudinal portion of the rod. Structure is provided for compressing the chevron packing rings against the mounting gland center web, such as by a packing gland that can be threadably secured to the mounting gland and to the end of the stuffing box.

The explosionproof sealing structure comprises a rigid non-electrically conductive polymeric flame path sealing material forming a plug extending from the mounting gland center web towards the cavity end of the mounting gland. Preferably, the plug substantially fills the cavity. The explosionproof sealing structure can further include a jam nut disposed in the flame path seal material that is secured to the metallic center rod and projections on at least one cavity wall of the cavity for mechanically engaging the flame path seal material.

The structure for preventing longitudinal movement of the explosionproof capacitance probe in one embodiment is the explosionproof sealing structure previously described.

The foregoing probes and probe bodies reduce or eliminate the cold flow of the insulating sheath surrounding a conductive probe rod. In addition, the cold flow of insulating material (commonly PTFE), is reduced or eliminated in accordance with the present invention. In one embodiment, the end of the PTFE sheath housed in the mounting gland has a 90° flange that is formed by bending a flanged sheath to 90° when secured within the mounting gland to engage the interior of a stuffing box. The stuffing box contains nested chevron packing rings and chevron stack end rings that are squeezed together and deformed to conform to the stuffing box cavity and produce a pressure activated seal between the polymer and the metal. The probe of the present invention withstands higher pressures without the need for periodic retorquing.

In another embodiment of the present invention, a flame path seal-off is made integral to the gland assembly thereby making the capacitance probe useful in explosionproof applications.

Each of these two embodiments of the present invention result in a lower intrinsic capacitance than those of existing probes. These lower intrinsic capacitances are easier to offset in the connected circuitry.

BRIEF DESCRIPTION OF THE DRAWINGS

FIG. 2 is a sectional view of one embodiment of the present invention;

FIG. 3 is an exploded sectional view of the embodiment of FIG. 2;

FIG. 4 is a sectional view of a second embodiment of the present invention;

FIG. 5 is an exploded sectional view of the embodiment of FIG. 4;

FIG. 6 is a top perspective view of a chevron packing ring of the type used in the present invention; and FIG. 7 is a bottom perspective view of a chevron packing ring of the type used in the present invention.

DETAILED DESCRIPTION OF THE PREFERRED EMBODIMENTS

Figure 1:
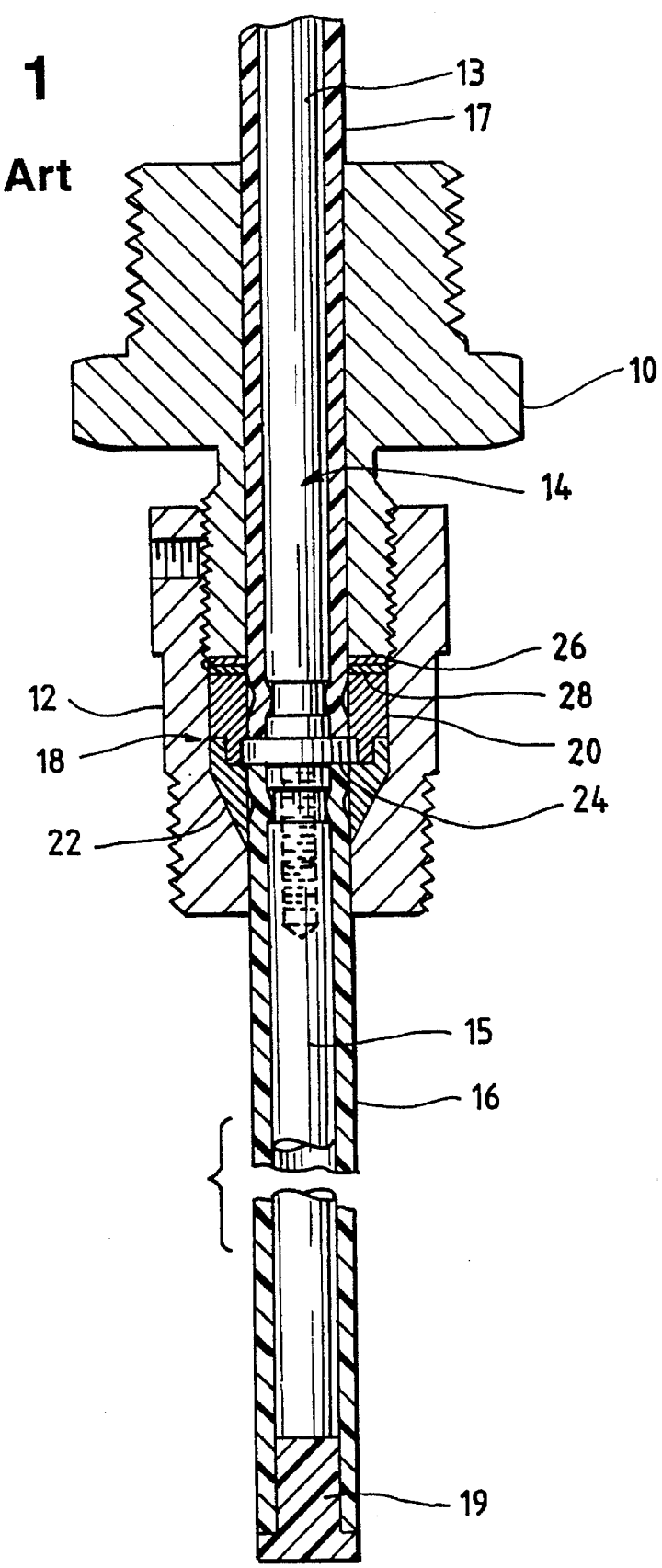
FIG. 1 is a sectional view of a prior art capacitance probe.

Referring to FIGS. 2 and 3, a high pressure, leak resistant capacitance probe 11 in accordance with the invention is illustrated. Capacitance probe 11 includes a probe body 21 and a conductive probe rod or center rod 40. Probe body 21 defines a through bore in which probe rod 40 is housed. Probe body 21 includes a mounting gland 30, a packing gland 60 and other components as hereinafter described. Unless otherwise noted, all components of probe 11 are axially symmetrical about the longitudinal centerline of probe 11. Cylindrical mounting gland 30 has outer lower threading 32, outer upper threading 34 and inner upper threading 35. Lower threading 32 is for mounting the capacitance probe in the vessel (not shown). Gland 30 may have a hexagonal longitudinal outer surface to facilitate mounting in a vessel. Upper threading 34 is used to mount the capacitance probe in an electronic housing (not shown). Inner upper threading 35 mates with threading 35 ' of packing gland 60. A through bore 36 extends through the length of mounting gland 30. Gland 30 defines a cylindrical stuffing box 38 having a common axis with bore 36 and a larger radius than bore 36 extends through the upper portion of mounting gland 30.

Center rod 40, fabricated of conductive metal, is used as the center plate of the coaxial capacitor. Center rod 40 includes a circumferential groove 41 that extends around the entire circumference of center rod 40 where indicated. Center rod 40 is electrically insulated from mounting gland 30 as hereinafter described. A lower sheath 42 insulates center rod 40 from mounting gland 30. Lower sheath 42 is made of an appropriate insulating polymer, such as PTFE. A solid PTFE cap or plug 43 insulates the end of center rod 40 and is suitably joined to lower sheath 42, such as by thermal joining. Lower sheath 42 has a flanged end 44 perpendicular to the length of lower sheath 42. When placed in mounting gland 30, flanged end 44 of sheath 42 engages bottom 38a of stuffing box 38.

PTFE flanged end 44 is thermally preformed in a jig from a PTFE tube to form a PTFE tube having about a 75° flange. It is difficult to manufacture flanged end 44 at precisely a 90° angle from the rest of lower sheath 42 from PTFE tubing. Therefore, flanged end 44 is not bent all the way to a 90° angle but rather is formed at an initial angle, e.g., 75° (i.e., forming a 105° angle between lower sheath 42 and flanged end 44). When the capacitance probe is assembled, compression on flanged end 44 is achieved by tightening packing gland 60 in mounting gland 30 to complete the 90° angle bend. When flanged end 44 is bent at 90° from lower sheath 42, the outer diameter of flanged end 44 fits snugly within the inner diameter of stuffing box 38. Alternatively, a prefabricated PTFE tube having a 90° end flange could be used.

Center rod 40 is placed in lower sheath 42 and then through bore 36 of mounting gland 30. Chevron packing rings 46 made of PTFE are placed around center rod 40 and are used to provide a positive seal because they are deformed under compression due to their geometry. Chevron packing rings 46 are of the type commonly used as valve packing. Chevron stack end rings 48 and 50 provide a planar surface to engage end 44 and a compression washer 52 located above chevron stack end ring 50.

Referring to FIGS. 6 and 7, a chevron packing ring 46 of the type used in the present invention is illustrated. Chevron packing ring 46 includes a top side 118 and a bottom side 120. Top side 118 is tapered in an upward direction. Bottom side 120 is also tapered in an upward direction. The shape of top side 118 and bottom side 120 are reciprocating, i.e., chevron packing rings 46 are stacked by placing the bottom side 120 of one chevron packing ring 46 directly on top of the top side 118 of a second chevron packing ring 46. Upon compression, both top side 118 and bottom side 120 tend to flatten. As a result, inside 122 of chevron packing ring 46 is urged towards center rod 40 in stuffing box 38. Similarly, outside 124 of chevron packing ring 46 is urged outward against mounting gland 30.

Compression washer 52 is made from a dense, nonconductive material, e.g., compressed fiber or G. E. Ultem 1000. Compression washer 52 is located relative to center rod 40 just below groove 41. A metallic retaining washer 54 is a split ring that surrounds center rod 40 in groove 41. Retaining washer 54 is larger in outer diameter than the inner diameter of packing gland 60 and the diameter of bore 36 to maintain center rod 40 retention in case of gland following washer 58 failure. Next, an outside washer 56, which may be made of the same material as compression washer 52, is placed about retaining washer 54. A gland following washer 58, which may be made from the same material as compression washer 52 and outside washer 56, is placed around center rod 40. Gland following washer 58 provides a bearing surface for a packing gland 60. Upper sheath 62 (also made of PTFE) is then placed around center rod 40 to provide electrical isolation from packing gland 60 when packing gland 60 is threadably tightened within mounting gland 30.

Finally, packing gland 60 is placed over center rod 40 and upper sheath 62. Packing gland 60 is then threaded into the upper portion of stuffing box 38. As packing gland 60 is tightened, it pushes downward on gland following washer 58. Gland following washer 58 in turn pushes down on retaining washer 54 and outside washer 56. Because retaining washer 54 is located in groove 41, retaining washer 54 urges center rod 40 downward. Retaining washer 54 and outside washer 56 also urge compression washer 52 downward into upper end chevron packing ring 50. Chevron packing rings 46 are spread thereby creating an effective seal. End 44 of lower sheath 42 is maintained against the lower portion of stuffing box 38. In this manner, the capacitance probe is sealed between the center rod 40 and mounting gland 30 and electrically insulated from mounting gland 30.

Cold flow of the PTFE of the probe is reduced or eliminated because there is no cavity into which the PTFE can flow. Moreover, the only PTFE portion that is compressed is flanged end 44 of lower sheath 42. The hydrostatic end forces, however, tend to relieve this compression to reduce any possibility of cold flow of the PTFE. In prior art capacitance probes, the hydrostatic end forces contributed to compression of the PTFE in some areas thereby increasing the likelihood of cold flow.

In addition to providing an effective seal, capacitance probe 11 effectively retains center rod 40 without permitting longitudinal movement of rod 40 with respect to probe body 21. Center rod 40 is retained in position because retaining washer 54 engages groove 41 of center rod 40. Therefore, center rod 40 moves vertically only to the extent that retaining washer 54 moves vertically. Because retaining washer 54 engages gland following washer 58 and gland following washer 58 is maintained in place by threaded packing gland 60, center rod 40 cannot move relatively vertically upward with respect to probe body 21. The engagement of end 44 against the lower portion of stuffing box 38, in combination with the elimination of the cold flow of the PTFE, prevents any relative downward vertical movement of center rod 40 with respect to probe body 21.

Because of the shorter coaxial length of center rod 40 and glands 30 and 60, the larger diameter of the dielectric portion (i.e., that portion between center rod 40 and mounting gland 30) of probe 11 and the larger separation between retaining washer 54 and packing gland 60, (as compared to the separation between metallic washer 24 and packing gland 10 of FIG. 1) as compared to existing capacitance probes, intrinsic probe capacitance is reduced significantly over that of existing capacitance probes. Because the present invention has a lower intrinsic probe capacitance, more accurate and reliable liquid level measurements are obtained.

Another embodiment of the present invention can be used in explosionproof applications. Referring to FIG. 4, an explosionproof capacitance probe 66 in accordance with the invention is illustrated. Probe 66 includes a probe body 67 and a center rod or probe rod 68. Probe body 67 includes a cylindrical mounting gland 70 having lower threading 72 and upper threading 74. Lower threading 72 is for mounting the capacitance probe in the vessel (not shown). Upper threading 74 is used to mount the capacitance probe in an electronic housing (not shown). A through bore 76 extends through the length of mounting gland 70. A cylindrical stuffing box 78 defines an enlarged bore portion 76' and thus has a common axis with bore 76 and a larger radius than bore 76 defined by and extending through the lower part of mounting gland 70. The lower portion of stuffing box 78 defined by mounting gland 70 is threaded to receive a packing gland 80.

A cylindrical threaded cavity 82 having projections from the wall thereof, in this embodiment truncated threading 83, is provided. Cavity 82 defines an enlarged bore portion 76" and thus has a common axis with bore 76 and a larger radius than bore 76 defined by and extending through the upper part of mounting gland 70. A retained center web 84 separates threaded cavity 82 and stuffing box 78. Center rod 68 of the present embodiment comprises a sensing rod 86 and a threaded rod 88 that is threaded into sensing rod 86. The portion of threaded rod 88 that sits within retained center web 84 is not threaded.

Although in this embodiment the center rod is made of two pieces, the center rod could be a single piece. The advantage of having two separate pieces is that sensing rod 86 has a larger radius than threaded rod 88. Because the radius of the vessel is substantially larger than the radius of the center rod, a larger center rod radius yields more accurate capacitance measurements. If the entire center rod were to have this larger radius, the probe would have an increased intrinsic capacitance. Thus, threaded rod 88 has a relatively smaller radius while sensing rod 86 has a larger radius.

A high density, nonconductive top washer 90 which can be constructed from, e.g., compressed fiber or G. E. Ultem 1000, and having a clearance hole for threaded rod 88, is placed within stuffing box 78 against retained center web 84. A metallic inside washer 92 is placed next to top washer 90. An outside washer 94 which can be made of the same material as top washer 90 encircles inside washer 92. Bottom washer 96 which can be made of the same material as top washer 90 and outside washer 94 is placed next to inside washer 92 and outside washer 94. Bottom washer 96 has a clearance hole to accommodate sensing rod 86. Metallic inside washer 92 is retained by a dense non-conductive material with high shear resistance providing excellent static load deformation resistance to developed hydrostatic end forces. This resistance is enhanced by the rigidity of the integral flame path seal-off assembly as described below. Chevron packing rings 98 are placed around sensing rod 86 as are chevron stack end rings 100 and 102. Chevron stack end rings 100 and 102 provide a planar surface to engage bottom washer 96 and an end 104 of a sheath 106, respectively.

Sheath 106 insulates sensing rod 86. Sheath 106 can be made of PTFE or a similar polymer. A solid PTFE cap 107 insulates the end of sensing rod 86 and is joined to sheath 106 thermally. End 104 of sheath 106 is bent to an angle in the same manner that end 44 of sheath 42 of the previous embodiment is created. A metallic gland following washer 108 engages end 104. Finally, packing gland 80 is threaded into the lower portion of stuffing box 78.

Threaded rod 88 is screwed into sensing rod 86. A sheath ring 112, which may be made of PTFE, is then placed around threaded rod 88. At approximately the center of threaded cavity 82, a pair of jam nuts 114 are jam threaded onto threaded rod 88. Threaded cavity 82 is then filled with an acceptable flame path seal-off material 116 which generally will be a rigid non-electrically conductive polymeric material. Flame path seal-off material 116 may be Epoxy No. 2850 FT-FR mixed with Catalyst No. 11 both available from Emerson & Cuming, Dewey & Almy Chemical Division, W. R. Grace & Co., Canton, Mass., or another suitable cement or epoxy. Truncated threading 83 in threaded cavity 82 provides mechanical connection of flame path seal-off material 116 with gland 70. Jam nuts 114 disposed in material 116 prevent longitudinal movement of rod 88 relative to gland 70. Material 116 is preferably placed in cavity 82 in fluid form and thereafter suitably cured or solidified. This assures intimate and secure contact and attachment between material 116, cavity 82, rod 88 and jam nuts 114.

Sheath end 104 is held in flat compression by metallic gland following washer 108. Thus, the PTFE has no cavities available in which to cold flow. Moreover, hydrostatic end forces tend to relieve any PTFE compression at this point. Chevron packing rings 98 provide a tight seal that does not require periodic retorquing to compensate for cold flow.

Because packing gland 80 does not require retorquing, packing gland 80 may be located in areas not possible with existing probes. For example, packing gland 80 can be placed in the inside of the vessel.

A conductive wire 117 is suitably attached to mounting gland 70 and serves as a ground reference. A second conductive wire 119 is electrically connected to probe rod 68 and to an electronic circuit board (not shown). A washer 121 and a screw 123 facilitate the connection of wire 119 to probe rod 68.

Sensing rod 86 and threaded rod 88 are prevented from being ejected in the case of an explosion by flame path seal-off material 116 being engaged with truncated threading 83 of threaded cavity 82 and jam nuts 114. As a final safety, the inner diameter of retained center web 84 is considerably smaller than the diameter of jam nuts 114 and inside washer 92.

Whereas the present invention has been described with respect to specific embodiments thereof, it will be understood that various changes and modifications will be suggested to one skilled in the art and it is intended that the invention encompass such changes and modifications as fall within the scope of the appended claims.

What is claimed is:

1. A capacitance probe for use in a vessel, wherein the wall of the vessel is used as one plate of a coaxial capacitor, comprising:

a mounting gland having a longitudinal bore extending therethrough, said longitudinal bore having a nominal diameter and an enlarged portion, the enlarged portion defining a stuffing box and a stuffing box bottom;

a metallic center rod used as a center plate of the coaxial capacitor, said center rod extending through the bore of said mounting gland;

an insulating sheath surrounding a lower portion of said center rod, said insulating sheath having a flanged end that forms an angle of about 90° with the remainder of the insulating sheath, said flanged end extending into said stuffing box;

sealing means for sealing the stuffing box between the center rod and the mounting gland and for electrically insulating the center rod from the mounting gland; and means for preventing longitudinal movement of said center rod relative to said mounting gland.

2. The capacitance probe of claim 1 wherein said sealing means comprises a plurality of compression deformable chevron packing rings contained in said stuffing box coaxial to said bore and surrounding a longitudinal portion of said rod; and means for compressing said chevron packing rings against said flanged end of said insulating sheath.

3. The probe of claim 2 wherein said compressing means comprises a packing gland secured to the mounting gland and extending into said stuffing box.

4. The probe of claim 3 wherein said stuffing box is threaded to receive said packing gland.

5. The probe of claim 1 wherein said means for preventing longitudinal movement comprises:

a circumferential groove in said center rod where said rod is disposed in said stuffing box;

a retaining washer disposed in said circumferential groove, said retaining washer having a larger outer diameter than the nominal diameter of said bore.

6. The probe of claim 5 wherein said means for preventing longitudinal movement further comprises:

a gland following washer to engage said retaining washer; and a packing gland to compress said gland following washer towards said stuffing box bottom.

7. An explosionproof capacitance probe for use in a vessel, wherein the wall of the vessel is used as one plate of a coaxial capacitor, comprising:

a mounting gland having a longitudinal bore extending therethrough, said mounting gland at one end having a cavity coaxial to said bore and a stuffing box at the other end of said mounting gland coaxial to said bore and longitudinally spaced from said cavity by a mounting gland center web;

explosionproof sealing means for sealing the cavity to provide a flame path seal in said cavity;

a metallic center rod used as a center plate of the coaxial capacitor, Said center rod extending through said bore;

an insulating sheath surrounding a lower portion of said center rod;

means for sealing the stuffing box between the center rod and the mounting gland and for electrically insulating the center rod from the mounting gland; and means for preventing longitudinal movement of said center rod relative to said mounting gland.

8. The probe of claim 7 wherein said means for sealing the stuffing box comprises a plurality of compression deformable chevron packing rings contained in said stuffing box coaxial to said bore and surrounding a longitudinal portion of said rod; and means for compressing said chevron packing rings against said mounting gland center web.

9. The probe of claim 8 wherein said compressing means comprises a packing gland secured to the mounting gland and extending into said stuffing box.

10. The probe of claim 9 wherein said stuffing box is threaded to receive said packing gland.

11. The probe of claim 7 wherein said explosionproof sealing means comprises a rigid non-electrically conductive polymeric flame path sealing material forming a plug extending from the mounting gland center web towards the cavity end of the mounting gland.

12. The probe of claim 11 wherein the plug substantially fills the cavity.

13. The probe of claim 11 wherein said explosionproof sealing means further comprises:

a jam nut disposed in the flame path seal material and secured to the metallic center rod; and wherein said cavity has at least one cavity wall having projections thereon to mechanically engage said flame path seal material.

14. The probe of claim 11 wherein said flame path seal-off material is epoxy resin.

15. The probe of claim 1 wherein said sealing means is pressure activated.

16. The probe of claim 7 wherein said insulating sheath has a flanged end extending into said stuffing box.

17. The probe of claim 16 wherein said flanged end forms an angle of about 90° with the remainder of said insulating sheath.

18. A capacitance probe for use in a vessel, wherein the wall of the vessel is used as one plate of a coaxial capacitor, comprising:

a mounting gland having a longitudinal bore extending therethrough, said longitudinal bore having a nominal diameter and an enlarged portion, the enlarged portion defining a stuffing box and a stuffing box bottom;

a metallic center rod used as a center plate of a coaxial capacitor, said center rod extending through the bore of said mounting gland and having a circumferential groove where said center rod is disposed in said stuffing box;

an insulating sheath surrounding a lower portion of said center rod, said insulating sheath having a flanged end extending into said stuffing box;

a plurality of compression deformable chevron packing rings contained in said stuffing box coaxial to said bore and surrounding a longitudinal portion of said center rod;

a retaining washer disposed in said circumferential groove, said retaining washer having a larger outer diameter than the nominal diameter of said bore;

an outside washer surrounding said retaining washer;

a gland following washer to engage said retaining washer and said outside washer;

a compression washer disposed between said retaining washer and said plurality of packing rings; and a packing gland to compress said gland following washer towards said stuffing box bottom.

19. The probe of claim 18 wherein said flanged end forms an angle of about 90° with the remainder of said insulating sheath.

* * * * *